(12) United States Patent
McMaster

(10) Patent No.: US 6,843,986 B1
(45) Date of Patent: Jan. 18, 2005

(54) ATTRACTANT COMPOSITION FOR FISHING LURES

(76) Inventor: Stephen L. McMaster, P.O. Box 1041, Shasta Lake, CA (US) 96019

( * ) Notice: Subject to any disclaimer, the term of this patent is extended or adjusted under 35 U.S.C. 154(b) by 0 days.

(21) Appl. No.: 10/253,833

(22) Filed: Sep. 23, 2002

(51) Int. Cl.[7] ............................................... A01N 25/10
(52) U.S. Cl. ........................ 424/84; 424/442; 424/485; 424/523; 424/750; 424/754; 43/42.06
(58) Field of Search ................................ 424/439, 442, 424/484, 485, 84, 523, 754, 750; 43/42.06, 42.45, 44.99; 426/1

(56) References Cited

U.S. PATENT DOCUMENTS

| | | |
|---|---|---|
| 4,704,286 A | 11/1987 | Rittschof et al. |
| 4,887,376 A | 12/1989 | Sibley et al. |
| 4,901,466 A | 2/1990 | Davis |
| 4,927,643 A | 5/1990 | D'Orazio et al. |
| 4,998,370 A * | 3/1991 | Lawler et al. ............. 43/42.06 |
| 5,827,551 A | 10/1998 | Prochnow et al. |
| 6,010,720 A * | 1/2000 | Derrieu et al. ............. 424/486 |
| 6,190,654 B1 | 2/2001 | Hukee |

FOREIGN PATENT DOCUMENTS

| | | |
|---|---|---|
| GB | 2117242 | * 10/1983 |
| JP | 53-138886 | * 12/1978 |
| JP | 53138886 | * 3/1979 |

* cited by examiner

*Primary Examiner*—Neil S. Levy
(74) *Attorney, Agent, or Firm*—John Smith-Hill; Smith-Hill and Bedell

(57) ABSTRACT

An attractant composition for application to fishing lures is composed of about 10–45% bees wax and up to about 75 % menhaden oil.

2 Claims, 1 Drawing Sheet

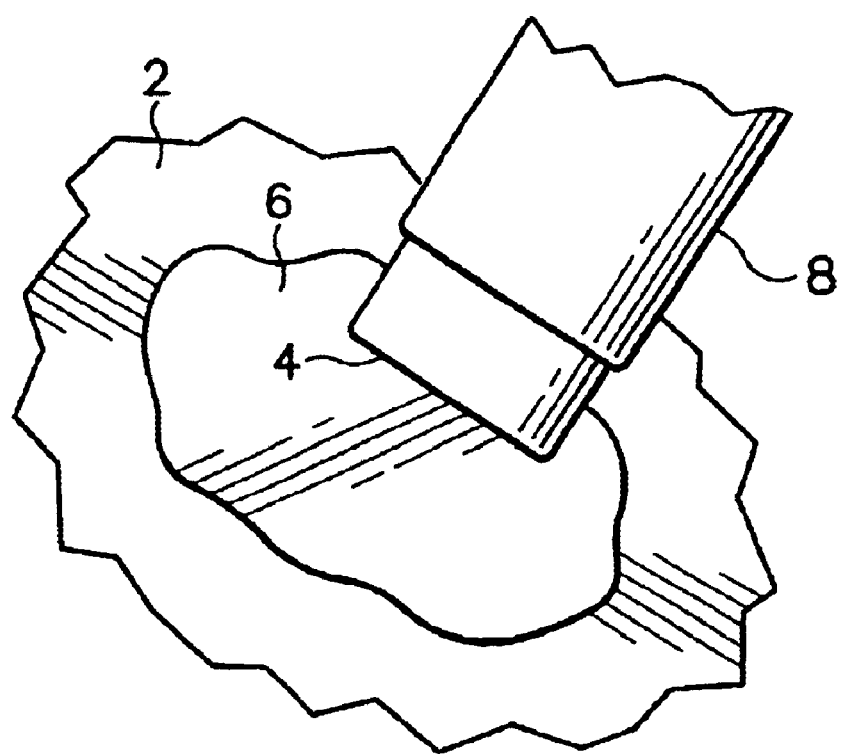

ATTRACTANT COMPOSITION FOR FISHING LURES

BACKGROUND OF THE INVENTION

This invention relates to an attractant composition for fishing lures, a method of treating a fishing lure, and fishing lures provided with a coating of an attractant composition.

Fishing is an extremely popular sport, and anglers go to a great deal of trouble and expense in order to gain an advantage over their prey. Numerous lures have been designed in order to increase the attractiveness of the lure to the fish. Further, in order to render a lure attractive not only to the visual sense but also to other senses of the fish, various kinds of flavored attractants have been proposed for application to fish lures.

SUMMARY OF THE INVENTION

According to a first aspect of the present invention there is provided an attractant composition comprising about 10–45% bees wax and up to about 75% menhaden oil.

According to a second aspect of the present invention there is provided a method of treating a fishing lure, comprising applying to the lure a solid attractant composition comprising about 10–45% bees wax and up to about 75% menhaden oil.

According to a third aspect of the present invention there is provided a fishing lure having a coating of an attractant composition comprising about 10–45% bees wax and up to about 75% menhaden oil.

BRIEF DESCRIPTION OF THE DRAWINGS

For a better understanding of the invention, and to show how the same may be carried into effect, reference will now be made, by way of example, to the accompanying drawings, the single FIGURE of which illustrates application of an attractant composition to a fishing lure.

All percentage values mentioned in the following description and claims are by volume.

DETAILED DESCRIPTION

A first composition embodying the present invention comprises 4.6% garlic juice, 4.6% menhaden oil, 64.5% corn oil and 26.3% bees wax. Garlic juice is commercially available from Garlic Research Labs. of Glendale, Calif.; menhaden oil is commercially available from Catch'n Bait Supply Co. of Brooksville, Fla. or Aylesworth Fish & Bait, Inc. of St. Petersburg, Fla.; corn oil is commercially available from various retail sources and bees wax is commercially available from various apiaries. The dominant odor of this composition is garlic.

The composition is prepared by heating the bees wax so that it just melts and separately heating the garlic; juice, menhaden oil and corn oil. The mixture of liquids is then added to the molten bees wax. Heating the liquids, before adding them to the bees wax avoids excessive cooling of the bees wax. The liquids and the bees wax are thoroughly mixed, and the blend is poured into appropriate containers. One type of container that is suitable is the #750 lip balm container available from Federal Package, Inc. Upon cooling, the composition solidifies and forms a solid rod of waxy material in a convenient dispensing tube.

The single FIGURE of the drawings illustrates waxy attractant composition 4 in the form of a rod held in a dispensing tube 8. The angler can hold the dispensing tube in his hand and apply the waxy material to a surface of a lure 2 as a coating 6. Because of the waxy consistency, the material can be applied as a thin coating on selected surfaces of the lure without dripping and wasting. A coating of the waxy material is deposited on the lure, regardless of whether the lure is made of plastic, rubber or metal.

When the lure is cast into the water, the waxy material, being water repellant, does not dissolve in the water and continues to cling to the lure over several casts. The bees wax ensures that the material remains firm and does not liquify even when the ambient temperature reaches 130° F. On a hot day, the water temperature will generally be substantially lower than the air temperature and accordingly immersion in the water will cool the lure and the attractant composition and increase the adhesion of the attractant composition to the lure. When the angler observes that, the coating has diminished substantially, he may apply more attractant without need to clean the lure of material from the previous application.

Another attractant composition embodying the invention comprises 73.7% menhaden oil and 26.3% bees wax by volume. This composition is prepared in similar fashion to the first composition. The dominant odor of this attractant composition is sardine. This composition may be modified and rendered particularly attractive to bait fish by adding a trace, e.g. less than 1%, of minced crickets.

A third attractant composition embodying the invention comprises 4.6% menhaden oil, 4.6% anise oil, 64.5% corn oil and 26.3% bees wax. This composition is prepared in similar fashion to the first composition. A suitable anise oil is available commercially from Xenex Laboratories, Inc. of Coquitlam, British Columbia, Canada. The anise oil may include a small quantity of minced raw crayfish, in which case this material has an odor of crayfish.

It has been found that these different attractant compositions are attractive to bass and other fish. The attractant composition may be applied not only to conventional lures, such as plugs, spoons and spinners, that are pulled through the water, but also to artificial flies, which usually remain on the surface of the water without sinking.

It will be appreciated that the invention is not restricted to the particular embodiment that has been described, and that variations may be made therein without departing from the scope of the invention as defined in the appended claims and equivalents thereof. For example, although each of the compositions mentioned above include about 27% bees wax, the composition may comprise as little as 10% bees wax or as much as 45% bees wax. It is preferred that the composition should contain from 15–40% wax, and it is more preferred that the composition should contain 15–35% wax. The composition should contain sufficient bees wax that it will remain solid under normal conditions of use built it should not contain so much bees wax that it is difficult to apply in a thin coating. Unless the context indicates otherwise, a reference in a claim to the number of instances of an element, be it a reference to one instance or more than one instance, requires at least the stated number of instances of the element but is not intended to exclude from the scope of the claim a structure or method having more instances of the element than stated.

What is claim is:

1. An attractant composition comprising about 10–45% bees wax, about 5% menhaden oil and about 5% garlic juice or anise oil, the balance being corn oil.

2. An attractant composition comprising about 10–45% bees wax, about 5% menhaden oil and about 5% anise oil, the balance being corn oil, and wherein the anise oil has fish particles dispersed therein.

* * * * *